United States Patent [19]

Simpson

[11] Patent Number: 5,756,099

[45] Date of Patent: May 26, 1998

[54] NATURAL ORGANIC TANNING SUNSCREEN COMPOSITIONS AND METHODS OF TREATMENT, TO REDUCE THE RISK OF SKIN CANCER CAUSED BY SUNLIGHT AND ULTRAVIOLET RADIATION (UVA AND UVB)

[75] Inventor: Jewel Simpson, 150 Tenth St., NE., Atlanta, Ga. 30309

[73] Assignee: Jewel Simpson, Atlanta, Ga.

[21] Appl. No.: 764,238

[22] Filed: Dec. 14, 1996

[51] Int. Cl.$^6$ ............................... A61K 7/40; A61K 7/42
[52] U.S. Cl. ............................... 424/195.1; 424/59
[58] Field of Search ............................... 424/59, 195.1

[56] References Cited

U.S. PATENT DOCUMENTS

| | | | |
|---|---|---|---|
| 4,906,457 | 3/1990 | Ryan | 424/59 |
| 5,290,605 | 3/1994 | Shapira | 424/439 |
| 5,545,402 | 8/1996 | Watkinson | 424/94.63 |
| 5,554,366 | 9/1996 | Rawlings | 424/78.03 |

*Primary Examiner*—Michael P. Woodward
*Assistant Examiner*—Mary K. Zeman

[57] ABSTRACT

A composition of a topical natural organic tanning sunscreen having medicinal properties utilized to reduce the risk of skin cancer and sunburn caused by sunlight and ultraviolet radiation (UVA and UVB) exposure. The chemical free tanning sunscreen composition, after application, provides the skin organ with a healthy tan within one to two hours when exposed to sunlight. Said composition consists of natural organic agents containing nutrients, minerals, chomophores and antioxidants which can be topically applied on the skin organ.

4 Claims, No Drawings

NATURAL ORGANIC TANNING SUNSCREEN COMPOSITIONS AND METHODS OF TREATMENT, TO REDUCE THE RISK OF SKIN CANCER CAUSED BY SUNLIGHT AND ULTRAVIOLET RADIATION (UVA AND UVB)

BACKGROUND FIELD OF THE INVENTION

A Natural organic sunscreen composition for external application which contains natural organic medicinal properties. (The term "organic" as used herein refers to the fact that no heat or chemical substances have been added to the natural sunscreen composition.),which protects the skin organ from skin cancer, sunburn, photo-aging and resistance from ultraviolet radiation, UVA and UVB rays. The natural organic sunscreen composition provides the exposed skin organ to immediate protection from the sun. The chemical free sunscreen composition provides the average skin types with a healthy tan within one to two hours in the bright sunlight.

BACKGROUND OF THE INVENTION

People do not have to sunbathe to suffer the negative effects of overexposure to ultraviolet radiation. Much of the skin damage can be done by day-to-day routine activities in the sunlight, because photobiologic reactions occur almost continuously both day and night. Sunlight has two types of harmful ultraviolet rays: UVA and UVB. The UVA rays are the sun's burning rays, the primary causes of sunburn and skin cancer, window glass blocks them. The UVB rays which pass through window glass, penetrate more deeply into the skin and appear to be the culprits in premature wrinkling; they also contribute to sunburn and skin cancer. Some scientists estimate that nearly 75 percent of the sun inflicted skin damage on the average person's skin over a lifetime is the result of just outdoors or sitting by a window. Many epidemiologic studies show a strong relationship between sunlight exposure and skin cancer. Another long-term hazard of ultraviolet radiation is photo-aging, this condition occurs when two types of protein substances clamped together breakdowns and thickens. This is what cause wrinkling. This kind of severe wrinkling is not due to old age but almost exclusively to photo-damage. Photo-damage can cause serious medical problems such as skin cancer.

Sunbathing for hours in the sunlight to acquire an "appealing" tan often results in long term hazards which are potentially dangerous to the human skin. The most common agents for sun protection are sunscreens. The increase in skin cancer over the years have caused the general public to rely heavy in the sunscreen products market. The sunscreen market has grown largely in recent years and new products are introduced annually. Sunscreen agents are commercially available to protect the skin from UVA radiation. In 1978 in writing its Sunscreen Monograph, the FDA established a list of Category I sunscreen products that were grand fathered as 'generally recognized as safe and effective.' Some include titanium dioxide and zinc oxide, in addition, to a few others. These agents scatter or reflect ultraviolet radiation. However, sunscreen compositions containing these agents are opaque, generally, unattractive in color, and are viewed as unacceptable for usage on more than just the nose or tops of the ears. Furthermore, these agents are very susceptible to rub-off resulting in little or no protection. The most common agents for sun protection are sunscreens. These agents exert their effects through chemical means, i.e., they absorb ultraviolet radiation, so that it cannot penetrate the dermis.

Most sunscreens present the user with several problems, for example, they must be on the surface of the skin at the time of sunlight exposure to be effective. One must anticipate being in the sun when using sunscreens. 'Cases of skin cancer caused by sun exposure are increasing'Guy Murdoch, il v. 77 "Consumers Research Magazine," July 94 p.10 (5). Other studies show that use of sunscreens in prolonged sunbathing may promote the development of skin cancer by inhibiting the body's natural immunity to abnormal skin growths' Jeffrey S. Dover and Kenneth A. Arndt, v. 271 JAMA, "Dermatology,"Jun. 1, 1994, p.1662 (2) 74F3905.

Furthermore, sunscreens are easily rubbed off or washed off by perspiration or swimming and can also be lost to skin penetration.

Sunscreen agents often cause skin and eye irritation primarily burning or stinging, respectively. This response can be more pronounced with a daily or almost daily use. Cases of skin cancer caused by sun exposure are increasing. There is still a continuing need to identify new chemical free sunscreen composition which will blend with the body's natural functions by providing natural protective means against UVA and UVB rays which causes skin cancer, sunburn and photo-aging.

Objects and Advantages

It is accordingly several objects and advantages of the present invention:

(a) to provide a natural organic sunscreen composition consisting of natural medicinal properties which will provide immediate protection from the sun for the average skin type;

(b) to provide a natural organic sunscreen composition which provides a preventive action against skin cancer, sunburn and photo-aging;

(c) to provide a natural organic sunscreen composition comprising natural medicinal properties by means of blending with the skin organs natural functions;

(d) to provide a natural organic sunscreen composition which provides an effective protective barrier against damaging UVA and UVB rays.

(e) to provide a natural organic sunscreen composition which is safe for all ages;

(f) to provide a natural sunscreen composition which can be applied to the skin's surface and penetrate through skin layers to provide antioxidants for skin protection in the epidermis layers;

(g) to provide a natural sunscreen composition which can be used as a natural moisturizer;

(h) to provide a natural organic sunscreen composition which will not rub-off, but is designed for deep skin penetration;

(i) to provide a natural organic sunscreen composition which will rapidly accelerate the melanization process in the average human skin types;

(j) to provide a natural organic sunscreen composition which will provide a healthy glowing skin and an "appealing" tan for the average human skin types within one to two hours.

(k) said composition will not irritate the skin organ.

It is still a further object of the present invention to provide a sunscreen composition which can be applied to incisions, cuts and opened wounds on the skin organ, whereby a healing process will be completed within three days.

3

These and other objects will become readily apparent from the detailed description which follows.

Detailed Description of the Invention

The natural organic sunscreen properties used in the present invention come from two plant type extracts that are grown on trees. both plant types are grown in the tropical lowlands and the subtropics.

The first plant is from the Palmae family and is from the drupe of the palmtree. The palmaes fossil record traces back to the Triassic Period. about 220 million years ago (American Encyclopedia). but did not enter trade until the middle of the 19th century. Some coconut trees grow to 98ft (30m) in height and may live as long as 100 years. These trees and their fruits are in bright sunlight year round. The fruit is a large single seeded drupe with a tan fibrous husk surrounding a hard stony brown shell. inside the shell is the fluid endosperm that nourishes the immature snow white embryonic spongy mass of tissue. The immature snow white embryonic spongy mass of tissue is part of the composition used in the present natural organic sunscreen invention.

The second plant type is from the family Caricaceae: The papaya which grows on slender palm like plants that may reach a height of 35 ft (11 cm). They develop quickly from seeds. They vary in shape from round too oval. The ripe fruit weighs from ¼ to 15 pounds and has smooth skin which ranges in colors from greenish-yellow to orange. The flesh may be yellow, orange or red, and it is filled with the fruit pea-sized black seeds.

It is the flesh of the papaya which is combined with the immature embryonic tissue of the drupe that is used in the natural organic sunscreen of the present invention.

SUMMARY OF THE INVENTION

The present invention relates to the composition of two tropical plant extracts when mixed together comprises medicinal properties which provides preventive action against skin cancer, sunburn and photo aging. This natural organic sunscreen composition leaves no skin irritation but can be used for healing cuts, and opened wounds. The said screen composition is effective in resisting the UVA and UVB wavelength ranges.

This composition consists of natural compound agents containing nutrients, minerals, chomophores and antioxidants which can be used externally on the human skin organ. The natural organic sunscreen agent in the present invention distinguishes itself from other sunscreen agents on the market because said composition when applied to the skin organ dissolves into a protective moisture substance that penetrates into the cells of the epidermis, whereby fortifying and intensifying the melanin pigment causing it to circulate and release the melanin pigment to the outer layer of skin when exposed to sunlight.

The present sunscreen invention provides immediate protection from the UVA and UVB wavelength rays, and a healthy tan appears within one to two hours. The Melanization process eliminates the long process of two- to-three-days wait for a tan. whereby that waiting period causes the damaging effects of ultraviolet wavelength rays which can result in skin cancer, sunburn, and photo-aging.

OPERATION OF THE INVENTION

The operation of the sunscreen agents useful in the present invention is to extract the soft mass of white tissue from the drupe and add it to the flesh of the papaya. The two substances are mixed together in a blender. Measurements are ¼ the amount of the papaya to ¾ measurements of the soft white tissue of the drupe. The composition develops into a smooth emollient substance within 15 minutes.

Once the two tropical plants are mixed, a peach color is developed and mixture can be placed in the refrigerater until it forms a solid base. Refrigeration is not required after said process. The mixed substance remains visible until it is externally applied to the skin organ, whereby it instantly liquefies into an emollient moisture which penetrates the surface of the dermis into the epidermis skin layers. The sunscreen composition penetrates into the skin layers through a conduction pathway which transmits the diffusion of a rapid accelerated melanin process. The melanin process provides a uniform layer of protective barriers in the skin organ whereby preventing the damaging effects of exposure to UVA and UVB rays. The beneficial effect of using the sunscreen composition in the present invention is continued protection against skin cancer, sunburn and photo-aging through external use of the nutrients, minerals, and antioxidants provided in said composition.

| Nutritional Value of the Papaya: | |
|---|---|
| Protein | 1.86 gm |
| Carbohydrate | 30 gm |
| Vitamins: | |
| A | 6122 IU (Beta Carotene) |
| B1 | .082 mg (Thiamine) |
| B2 | .097 mg (Riboflavin) |
| B6 | .058 mg (Pyridoxine) |
| C | 187 mg (ascorbic acid) |
| Niacin | 1.02 mg |
| Minerals: | |
| Calcium | 72 mg |
| Copper | 049 mg |
| Iron | 3 mg |
| Magnesium | 31 mg |
| Manganese | 033 mg |
| Phosphorus | 16 mg |
| Potassium | 780 mg |
| Sodium | 8 mg |
| Zinc | .22 mg |
| Lipids | |
| Total lipid (fat | .43 gm |
| Total saturated | .131 gm |
| Total unsaturated | .21 gm |
| Amino acids: | |
| Tryptophan | .024 gm |
| Threonine | .033 gm |
| Leucine | 049 gm |
| Lysine | 076 gm |
| Methionine | .006 gm |
| Phenylalanine | .027 gm |
| Tyrosine | .015 gm |
| Valine | .03 gm |
| Arginine | .03 gm |
| Histidine | .015 gm |
| Alanine | 043 gm |
| Aspartic acid | .149 gm |
| Glutamic acid | .1 gm |
| Glycine | .055 gm |
| Nutritional Value of the Coconut: | |
| Vitamins: | |
| B1 | .04 |
| B2 | .02 |
| B6 | .035 |
| Niacin | .4 mg |
| Pantothenic acid | .16 mg |

-continued

| | |
|---|---|
| Folic acid | .031 mcg |
| C | .2 mg |
| E | .8 IU |
| Minerals: | |
| Calcium | 10 mg |
| Copper | .368 mg |
| Iron | 1.4 mg |
| Magnesium | 37 mg |
| Manganese | 1.05 mg |
| Phosphorus | 76 mg |
| Potassium | 205 mg |
| Sodium | 18 mg |
| Zinc | .88 mg |
| Lipids: | |
| Total lipids (fat) | 28.2 mg |
| Total saturated | 24.3 gm |
| Total unsaturated | 2 |
| Amino Acids: | |
| Tryptophan | 031 gm |
| Threonine | 097 gm |
| Isoleucine | 105 gm |
| Leucine | 198 gm |
| Lysine | .118 gm |
| Methionine | .05 gm |
| Cystine | .053 gm |
| Phenylalanine | .135 gm |
| Tyrosine | .082 gm |
| Valine | 162 gm |
| Arginine | 437 gm |
| Histidine | 062 gm |
| Alanine | .136 gm |
| Aspartic acid | .26 gm |
| Glutamic acid | .609 gm |
| Glycine | .126 gm |

-continued

| | |
|---|---|
| Proline | .11 gm |
| Serine | .138 gm |

What is claimed is:

1. A natural, organic topical tanning sunscreen composition for reducing the risk of-skin cancer caused by sunlight or Ultraviolet radiation (UVA and UVB) exposure, consisting essentially of a mixture of the flesh of the papaya and the embryonic, spongy mass of tissue of the coconut in a proportional ratio of 1:3.

2. The process of preparing the natural, organic, topical tanning sunscreen composition according to claim 1 comprising the steps of: Extract the embryonic, spongy mass of tissue of the coconut from the drupe and add it to the flesh of the papaya in a proportional ratio 1:3 of the said papaya to the said coconut to mix or blend in a blender to form a smooth, peach colored emollient substance and mixing or blending for up to 15 minutes.

3. A method for treating the skin organ to reduce the risk of sunburn caused by sunlight and ultraviolet radiation (UVA and UVB) exposure with said composition as a tanning sunscreen according to claim 1 comprising applying a sufficient amount of said composition topically to the skin organ.

4. A method for treating the skin organ to reduce the risk of photo-aging of the skin organ through the exposure of sunlight or ultraviolet radiation with said composition according to claim 1 by applying a sufficient amount of said composition topically to the skin organ.

* * * * *